United States Patent
Ishida et al.

(10) Patent No.: US 9,956,246 B2
(45) Date of Patent: May 1, 2018

(54) SOLID INGESTIBLE COMPOSITION COMPRISING A FAT GLOBULE MEMBRANE COMPONENT AND WATER-SOLUBLE DIETARY FIBER

(71) Applicant: KAO CORPORATION, Tokyo (JP)

(72) Inventors: Yuki Ishida, Mishima (JP); Youichi Arai, Kawaguchi (JP); Yasushi Shioya, Toshima (JP)

(73) Assignee: KAO CORPORATION, Tokyo (JP)

( * ) Notice: Subject to any disclaimer, the term of this patent is extended or adjusted under 35 U.S.C. 154(b) by 0 days. days.

(21) Appl. No.: 15/308,801

(22) PCT Filed: Jun. 27, 2014

(86) PCT No.: PCT/JP2014/067216
§ 371 (c)(1),
(2) Date: Nov. 3, 2016

(87) PCT Pub. No.: WO2015/198482
PCT Pub. Date: Dec. 30, 2015

(65) Prior Publication Data
US 2017/0157166 A1 Jun. 8, 2017

(51) Int. Cl.
| | |
|---|---|
| A61K 31/734 | (2006.01) |
| A61K 9/00 | (2006.01) |
| A61K 35/20 | (2006.01) |
| A61K 47/36 | (2006.01) |
| A61K 9/20 | (2006.01) |
| A61K 31/688 | (2006.01) |
| A23L 33/10 | (2016.01) |

(52) U.S. Cl.
CPC ............ *A61K 31/734* (2013.01); *A23L 33/10* (2016.08); *A61K 9/0056* (2013.01); *A61K 9/20* (2013.01); *A61K 31/688* (2013.01); *A61K 35/20* (2013.01); *A61K 47/36* (2013.01)

(58) Field of Classification Search
CPC ........... A61K 35/20; A61K 47/36; A61K 9/20
See application file for complete search history.

(56) References Cited

U.S. PATENT DOCUMENTS

| | | | |
|---|---|---|---|
| 8,268,360 B2 * | 9/2012 | Ota | A61K 38/011 424/520 |
| 2003/0107149 A1 | 6/2003 | Yang et al. | |
| 2009/0087537 A1 * | 4/2009 | Hiroe | A23C 9/1544 426/577 |
| 2009/0117198 A1 | 5/2009 | Kawakami et al. | |
| 2011/0171317 A1 | 7/2011 | Kawakami et al. | |
| 2012/0052129 A1 * | 3/2012 | Ota | A61K 38/011 424/520 |
| 2012/0058194 A1 * | 3/2012 | Vaya | A61K 9/5026 424/494 |

FOREIGN PATENT DOCUMENTS

| | | | | |
|---|---|---|---|---|
| EP | 1991248 B1 * | 4/2012 | ........... | A61K 31/195 |
| JP | 7-236451 A | 9/1995 | | |
| JP | 2005-528328 A | 9/2005 | | |
| JP | 2006-158232 A | 6/2006 | | |
| JP | 2007-131550 A | 5/2007 | | |
| JP | 2007-320901 A | 12/2007 | | |
| JP | 2009-221157 A | 10/2009 | | |
| JP | 2010-59155 A | 3/2010 | | |
| JP | 2014-50336 A | 3/2014 | | |
| JP | 2014-60987 A | 4/2014 | | |
| JP | 2014-129285 A | 7/2014 | | |
| JP | 5816760 B1 | 11/2015 | | |
| JP | 5816761 B1 | 11/2015 | | |
| JP | 2016-26491 A | 2/2016 | | |
| JP | 2016-123306 A | 7/2016 | | |
| JP | 2016-123322 A | 7/2016 | | |
| JP | 2016-123323 A | 7/2016 | | |
| WO | WO 2007100668 A2 * | 9/2007 | ........... | A61K 31/195 |
| WO | 2013/080911 A1 | 6/2013 | | |

OTHER PUBLICATIONS

Susumu Miura: Food Style 21, vol. 13, No. 2, Total 6 Pages, (2009), (with English Translation).
International Search Report dated Sep. 22, 2014 in PCT/JP14/067216 Filed Jun. 27, 2014, 4 pages.

* cited by examiner

Primary Examiner — Christopher R Tate
Assistant Examiner — Aaron J Kosar
(74) Attorney, Agent, or Firm — Obon, McClelland, Maier & Neustadt, L.L.P.

(57) ABSTRACT

A solid composition comprising the following components (A) and (B): (A) from 20 to 65 mass % of a fat globule membrane component; and (B) from 0.2 to 4 mass % of a water-soluble dietary fiber having a weight average molecular weight of 10,000 or more.

16 Claims, No Drawings

SOLID INGESTIBLE COMPOSITION COMPRISING A FAT GLOBULE MEMBRANE COMPONENT AND WATER-SOLUBLE DIETARY FIBER

FIELD OF THE INVENTION

The present invention relates to a solid composition.

BACKGROUND OF THE INVENTION

It is known that a fat globule membrane component (Milk-fat Globule Membrane) is a membrane component that coats milk fat globules secreted from the mammary gland and is contained at a large amount in a milk complex lipid-rich fraction, such as butter milk or butter serum (Non Patent Literature 1). It is reported that the fat globule membrane component has many physiological functions, such as a motor function improvement effect of, for example, muscle, a visceral fat accumulation inhibitory effect, and an effect of increasing in and suppressing a decrease in a blood adiponectin level, in addition to a function of dispersing fat into milk (Patent Literatures 1 and 2).

In recent years, the number of metabolic syndrome or locomotive syndrome patients has markedly increased, resulting in a major social problem. In this regard, the fat globule membrane component having physiological functions as described above is expected to be widely used.

To effectively obtain the physiological functions of the fat globule membrane component, a solid composition form such as a tablet that can be continuously taken with ease for a long time is desirable; however, a tablet containing a fat globule membrane component that is currently sold contains the fat globule membrane component at extremely low concentration. To obtain the physiological functions of the fat globule membrane component, the amount of the fat globule membrane component (in terms dry matter) is considered to be preferably 10 mg/60 kg body weight or more per day for an adult individual (Patent Literature 1). For this reason, it is demanded that the fat globule membrane component is blended at high concentration so that the amount of the solid composition ingested per one time is set to be small.

Patent Literature 1: JP 2010-59155 A
Patent Literature 2: JP 2007-320901 A
Non Patent Literature 1: Susumu Miura, FOOD STYLE 21, 2009

SUMMARY OF THE INVENTION

The present invention provides a solid composition comprising the following components (A) and (B):
(A) from 20 to 65 mass % of a fat globule membrane component; and
(B) from 0.2 to 4 mass % of a water-soluble dietary fiber having a weight average molecular weight of 10,000 or more.

DETAILED DESCRIPTION OF THE INVENTION

However, as a result of the present inventors' studies, it was revealed that difficulty is encountered in blending a fat globule membrane component into a solid composition at such a high concentration that physiological functions can be expected only by a small single ingestion. That is, it was revealed that when the concentration of the fat globule membrane component increases, the composition had a dry texture and was crumbly and poor in the melt-in-the-mouth texture, and contrary to expectations, milk flavor intrinsic to the fat globule membrane component is difficult to be sensed in some cases.

Therefore, the present invention is intended to provide a solid composition which is easily ingested while containing a high concentration of the fat globule membrane component and has a favorable texture and flavor.

The present inventors conducted extensive studies, and as a result, they found that when a predetermined water-soluble dietary fiber is combined with the fat globule membrane component, it is possible to obtain a solid composition which has a favorable texture and flavor, in which a dry texture is reduced and a melt-in-the-mouth texture is improved so as to easily ingest the composition regardless of containing the fat globule membrane component at high concentration, and in which a milk flavor intrinsic to the fat globule membrane component is increased and a moderate sour taste is also sensed.

According to the present invention, it is possible to provide a solid composition which has favorable texture and flavor, in which a dry texture is reduced and a melt-in-mouth texture is improved so as to easily ingest the composition although containing a fat globule membrane component at high concentration, and in which a favorable milk flavor derived from the fat globule membrane component and a favorable soar taste are sensed. It is possible to ingest an amount of the fat globule membrane component necessary for exhibiting the physiological effects thereof by ingesting only a small amount of the solid composition of the present invention, and thus the sufficient effect of the fat globule membrane component can be expected over a long period of time.

The fat globule membrane component (A) used in the present invention is defined as a membrane coating milk fat globules and a mixture of components constituting the membrane. About half of dry weight of the fat globule membrane is generally composed of lipids, and as the lipids, it is known to include a triglyceride, a phospholipid, and a glycosphingolipid (Susumu Miura, FOOD STYLE 21, 2009 and Keenan T W, Applied Science Publishers, 1983, pp 89 to pp 130). As the phospholipid, it is known to include a sphingophospholipid such as sphingomyelin, and a glycerophospholipid such as phosphatidyl choline or phosphatidyl ethanolamine.

In addition, as a component other than the lipid, it is known to include glycoprotein called milk mucin (Mather, Biochim Biophys Acta, 1978).

A content of lipid in the fat globule membrane component (A) used in the present invention is preferably 10 mass % (hereinafter, simply referred to as "%") or more, more preferably 20% or more, still more preferably 30% or more, and the content is preferably 100% or less, more preferably 90% or less, still more preferably 60% or less, from the viewpoint of the physiological effects. In addition, the content of lipid in the fat globule membrane component is preferably from 10 to 100%, more preferably from 20 to 90%, still more preferably from 30 to 60%.

A content of phospholipid in the fat globule membrane component (A) is preferably 5% or more, more preferably 8% or more, still more preferably 10% or more, still more preferably 15% or more, and the content is preferably 100% or less, more preferably 85% or less, still more preferably 70% or less, still more preferably 60% or less, from the viewpoint of the physiological effects. In addition, the content of phospholipid in the fat globule membrane component is preferably from 5 to 100%, more preferably from 8 to 90%, still preferably from 10 to 70%, still mere preferably from 15 to 60%.

Further, the fat globule membrane component (A) preferably contains sphingomyelin as a phospholipid from the viewpoint of the physiological effects. A content of sphingomyelin in the fat globule membrane component is preferably 1% or more, more preferably 2% or more, still more preferably 3% or more, and from the viewpoint of flavor and handleability, the content is preferably 50% or less, more preferably 30% or less, still more preferably 25% or less, still mote preferably 20% or less. In addition, the content of sphingomyelin in the fat globule membrane component is preferably from 1 to 50%, more preferably from 2 to 30%, still more preferably from 3 to 25%, still more preferably from 3 to 20%.

From the same viewpoints, a content of sphingomyelin in the total, phospholipids of the fat globule membrane component is preferably 3% or more, more preferably 5% or more, still more preferably 10% or more, still more preferably 15% or more, and the content is preferably 50% or less, more preferably 40% or less, still more preferably 35% or less, still more preferably 30% or less. In addition, the content of sphingomyelin in the total phospholipids of the fat globule membrane component is preferably from 3 to 50%, more preferably from 5 to 40%, still more preferably from 10 to 35%, still more preferably from 15 to 30%.

Incidentally, in the present specification, the contents of lipid, phospholipid, and sphingomyelin in the fat globule membrane component and the content of sphingomyelin in the total phospholipids of the fat globule membrane component are a mass proportion with respect to a dry matter of the fat globule membrane component.

The fat globule membrane component (A) described above may be obtained from raw material milk by a known method such as a centrifugation method or an organic solvent extraction method. For example, a preparation method of a fat globule membrane component described in JP 3-47192 A may be used. In addition, methods described in, for example, JP 3103218 B2 and JP 2007-85535 A may be used. Moreover, a fat globule membrane component which is purified by techniques such as dialysis, ammonium sulfate fractionation, gel filtration, isoelectric precipitation, ion-exchange chromatography, and solvent fractionation to have an increased purity may be used.

Incidentally, the form of the fat globule membrane component (A) is not particularly limited, and the form may be any one of liquid, semisolid (for example, paste), and solid (for example, powder, solid form, or granule) at room temperature (from 15 to 25° C.). These may be used alone or in combination of two or more kinds thereof.

Examples of the raw material milk of the fat globule membrane component (A) include cow milk and goat milk. Among these, Cow milk is preferable from the viewpoint that it is commonly consumed in diet and has low price. In addition, the raw material milk includes not only milk, such as raw milk, whole milk powder, or processed milk, but also dairy products. Examples of the dairy products include butter milk, butter oil, butter serum, and whey protein concentrate (WPC).

Butter milk is obtained during the production of fat granules from cream obtained by centrifugation of, for example, cow milk. Since a large amount, of the fat globule membrane component is contained in the butter milk, the butter milk may be directly used as the fat globule membrane component. Likewise, since a large amount of the fat globule membrane component is also contained in butter serum obtained during the production of butter oil, the butter serum may be directly used as the fat globule membrane component.

As the fat globule membrane component (A), commercially available products may also be used. Examples of the commercially available products include "BSCP" produced by MEGGLE JAPAN CO., LTD., "Milk Ceramide MC-5" produced by Snow Brand Milk Products Co., Ltd., and "Phospholipid Concentrate Series (500, 700)" produced by New Zealand Milk Products Co., Ltd.

A content of the fat globule membrane component (A) in the solid composition of the present invention is from 20 to 65%; from the viewpoints of effectively exhibiting the physiological effects and of an ingestion form which enables ingestion in a small amount at a time, the content is preferably 25% or more, more preferably 30% or more, still more preferably 35% or more, still more preferably 40% or more, and from the viewpoint that stickiness and adhesion in the mouth during eating are less, the content is preferably 60% or less, more preferably 55% or less, still more preferably 50% or less. In addition, the content of the fat globule membrane component (A) in the solid composition is preferably from 20 to 60%, more preferably from 25 to 55%, still more preferably from 30 to 50%.

Further, from the viewpoint of effectively exhibiting the effects, a content of phospholipid in the solid composition of the invention is preferably 1% or more, more preferably 2% or more, still more preferably 3% or more, still more preferably 4% or more, and from the viewpoint that stickiness and adhesion in the mouth during eating are less, the content is preferably 60% or less, more preferably 50% or less, still more preferably 40% or less, still more preferably 30% or less. In addition, the content of phospholipid in the solid composition is preferably from 1 to 60%, more preferably from 2 to 50%, still more preferably from 3 to 40%, still more preferably from 4 to 30%.

Further, a content of sphingomyelin in the solid composition of the present invention is preferably 0.5% or more, more preferably 0.7% or more, still more preferably 1% or more from the viewpoint of the physiological functions, and the content is preferably 3.5% or less, more preferably 3% or less from the viewpoint that stickiness and adhesion in the mouth during eating are less. In addition, the content of sphingomyelin in the solid composition is preferably from 0.5 to 35%, more preferably from 0.7 to 3.5%, still more preferably from 1 to 3%.

The contents of lipid and phospholipid in the fat globule membrane component or the solid composition may be measured by acid digestion, a colorimetric method, or thin-layer chromatography.

The weight average molecular weight of the water-soluble dietary fiber (B) used in the present invention is 10,000 or more. The term "weight average molecular weight" in this specification is a weight average molecular weight measured by gel permeation chromatography (GPC) measurement unless otherwise specified. The measurement of the weight average molecular, weight of the water-soluble dietary fiber by this GPC method is carried out according to the method described in Examples later.

When the water-soluble dietary fiber having a weight average molecular weight of 10,000 or more is combined with the fat globule membrane component, the texture and the flavor of the solid composition are excellent, and tablet-forming property in production of the solid composition becomes favorable, which is preferable.

From such a viewpoint, the weight average molecular weight of the water-soluble dietary fiber (B) is preferably 15,000 or more. In addition, from the viewpoint of flavor, the weight average molecular weight, is preferably 300,000 or less, more preferably 250,000 or less. The weight average molecular weight of the water-soluble dietary fiber (B) is preferably from 10,000 to 300,000, more preferably from 15,000 to 250,000.

A content of the water-soluble dietary fiber (B) in the solid composition of the present invention is from 0.2 to 4%; from the viewpoint of favorable crispy texture without dry texture during eating and favorable melt-in-the-mouth texture, the content is preferably 0.3% or more, more preferably 0.5% or more, and from, the viewpoint that moderate sour taste is sensed, the content is preferably 3% or less. In addition, the content of the water-soluble dietary fiber (B) in the solid composition is preferably from 0.3 to 4%, more preferably from 0.5 to 3%.

The content of the water-soluble dietary fiber in the solid composition of the present invention may be measured by the Prosky method (enzymatic-gravimetric method) and high performance liquid chromatography (enzymatic-HPLC method) described in Food Nutrition Labeling Standard System Vol. 3 (January, 2001, edited by Japan Health and Nutrition Food Association, pp. 46 to 51). At this time, in order to remove a dietary fiber derived from an insoluble solid matter, as described in the journal of Japan Society of Nutrition and Food Science, 46 (3) 244 (1933), the water-soluble dietary fiber may be fractionated using a glass filter (No. 2) into which Celite is put.

The viscosity of the water-soluble dietary fiber (B) used in the present invention is preferably from 20 to 300 mPa·s, more preferably from 50 to 300 mPa·s from the viewpoint of flavor. The term "viscosity" in this specification is a viscosity of an aqueous solution at 20° C., which is prepared by dissolving 10 g of the water-soluble dietary fiber in 90 g of ion water. The viscosity of the water-soluble dietary fiber may be measured by a B-type viscometer (100 revolutions/min).

Examples of the water-soluble dietary fiber include an acidic polysaccharide water-soluble dietary fiber such as alginic acid, carrageenan, polyglutamic acid, fucoidan, agaropectin, gum arabic, karaya gum, gellan gum, xanthan gum, or salts thereof; and a neutral polysaccharide water-soluble dietary fiber such as indigestible dextrin, guar gum, polydextrose, glucomannan, pullulan, water-soluble corn fiber, hemicellulose, soybean dietary fiber, or locust bean gum. These may be used alone or in combination of two or more kinds thereof. The salt of the acidic polysaccharide water-soluble dietary fiber is preferably an alkali metal salt, more preferably a potassium salt or sodium salt.

The water-soluble dietary fiber (B) is preferably sodium alginate, guar gum, or pullulan, more preferably guar gum or pullulan from the viewpoint of taste.

Alginic acid is a high-molecular-weight acidic polysaccharide that has, as a main constituent sugar, uronic acid (D-mannuronic acid and L-guluronic acid), which is a substance distributed in cell walls of brown algae, and one constituent unit has one carboxyl group. The weight average molecular weight of the alginic acid or a salt thereof used in the present invention is preferably from 20,000 to 80,000, more preferably from 30,000 to 60,000 from the viewpoint of flavor and physical properties.

Guar gum is a galactomannan polysaccharide having D-mannose as a main chain and D-galactose as a side chain. The guar gum may be a guar gum decomposition product obtained by partially hydrolysing guar gum using an enzyme (for example, galactomannanase) to reduce the viscosity thereof. The guar gum decomposition product is preferably a guar gum enzyme decomposition product that is a component having an energy conversion factor of 2, (kcal/g) defined in Sections 1) and 2) on Item 1 (partial revision of "Analysis Method of Nutrient Components in Nutrition Labeling Standards") of SyokuShinHatsu (Food New Development) No. 0217002 (Feb. 17, 2003) of Notification of New Development Food Sanitation Division Director of Planning Section of Pharmaceutical and Food Safety Bureau in Ministry of Health, Labour and Welfare.

The weight average molecular weight of the guar gum used in the present invention is preferably from 100,000 to 300,000, more preferably from 150,000 to 250,000 from the viewpoint of flavor and physical properties.

In addition, the weight average molecular weight of the guar gum decomposition product is preferably from 10,000 to 50,000, more preferably from 15,000 to 30,000 from the viewpoint of flavor.

Pullulan is a polysaccharide in which maltotriose is repeatedly bonded in a chain shape by an α-1,6 bond. It is known that pullulan is extracellularly produced by *Aureobasidum pullulans* that is one kind of black yeast.

The weight average molecular weight of pullulan used in the present invention is preferably from 30,000 to 100,000, more preferably from 40,000 to 85,000 from the viewpoint of flavor.

In the solid composition of the present invention, a mass ratio of the content of the water-soluble dietary fiber having a weight average molecular weight of 10,000 or more (B) in the solid composition to the content of the fat globule membrane component (A) in the solid composition, [(B)/(A)], is preferably 0.004 or more, more preferably 0.0075 or more, still more preferably 0.01 or more from the viewpoint of favorable crispy texture without dry texture during eating and favorable melt-in-mouth texture. In addition, from the viewpoint that moderate sour taste is sensed, the mass ratio is preferably 0.15 or less, more preferably 0.1 or less, still more preferably 0.08 or less. The range of such a mass ratio is preferably from 0.004 to 0.15, more preferably from 0.004 to 0.1, still more preferably from 0.004 to 0.08, still more preferably from 0.01 to 0.08.

In addition to the above-described components, the solid composition of the present invention may appropriately contain therein a mineral (for example, iron, zinc, chromium, selenium, manganese, molybdenum, copper, iodine, phosphorus, potassium, or sodium), a vitamin (for example, vitamin A, vitamin B1, vitamin B2, vitamin B6, vitamin B12, vitamin C, and folic acid, and salts or esters thereof), a sweetener (for example, a monosaccharide, an oligosaccharide, a sugar alcohol, or a synthetic sweetener), an acidulant (for example, citric acid, malic acid, tartaric acid, lactic acid, succinic acid, adipic acid, glucono-delta-lactone, gluconic acid, acetic acid, or fumaric acid), a flavor, a coloring agent, and a preservative, to the extent, that the effects of the present invention are not impaired.

The form of the solid composition of the present invention is not particularly limited as long as it remains solid at room temperature (from 15 to 25° C.). Examples of dosage form include capsules, granules, powders, tablets, pills, and troches. Among them, from the viewpoint of ease of ingestion, granules, tablets, or troches are preferable, chewable tablets or troches are more preferable, and chewable tablets are still more preferable. Further, when the solid composition is formulated into a tablet, the solid composition may also be formulated into a scored tablet having a cleavage line thereon.

When the solid composition is produced into such a dosage form, a carrier that is acceptable may be blended as necessary. Examples of the carrier include an excipient (for example, lactose, starches, crystalline cellulose, sucrose, light anhydrous silicic acid, or calcium hydrogen phosphate), a binder (for example, hydroxypropyl methylcellulose, hydroxypropylcellulose, gelatin, pregelatinized starch, polyvinylpyrrolidone, polyvinyl alcohol, methyl cellulose, or hydrogenated oil), a disintegrant (for example, carmellose, carmellose calcium, croscarmellose sodium, crospovidone, corn starch, or low substituted hydroxypropylcellulose), a lubricant (for example, calcium stearate, magnesium stearate, sucrose fatty acid ester, sodium stearyl fumarate, talc, or silicon dioxide), a corrigent (for example, stevia), a bulking filler, a surfactant, a dispersing agent, a buffer, a preservative, and a diluent.

The shape of the solid composition may be a round, tablet or various odd-shaped tablets having, for example, elliptic, oval, and square faces. In the case of a round tablet, from the viewpoint of easiness of taking thereof, the diameter of the round tablet is preferably from 5 to 15 mm.

In a case where the solid composition of the present invention is a tablet, the weight of each tablet is set to preferably from 0.1 to 2 g, more preferably from 0.3 to 1 g from the viewpoint of ease and effectiveness.

The solid composition of the present invention is produced by a common method without particular limitation. For example, the solid composition can be produced by preparing a mixture of the fat globule membrane component (A), the water-soluble dietary fiber having a weight average molecular weight of 10,000 or more (B), and an additive that is added as necessary, and subsequently subjecting the mixture to compression molding.

In the case of producing a tablet, a tableting machine that is commonly used, such as a rotary tableting machine or a single punch tableting machine, may be used.

The compression molding pressure during tableting is preferably about from 10 to 30 MPa, from the viewpoint of maintaining the hardness of a molded product or the viewpoint of the disintegration of the molded product, for example.

Regarding the above-described embodiment, the present invention further discloses the following compositions.

<1> A solid composition comprising the following components (A) and (B):
(A) from 20 to 65 mass % of a fat globule membrane component; and
(B) from 0.2 to 4 mass % of a water-soluble dietary fiber having a weight average molecular weight of 10,000 or more.

<2> The solid composition described in <1>, wherein a content of lipid in the fat globule membrane component (A) is preferably 10 mass % or more, more preferably 20 mass % or more, still more preferably 30 mass % or more; the content is preferably 100 mass % or less, more preferably 90 mass % or less, still more preferably 60 mass % or less; and the content is preferably from 10 to 100 mass %, more preferably from 20 to 90 mass %, still more preferably from 30 to 60 mass %.

<3> The solid composition described in <1> or <2>, wherein a content of phospholipid in the fat globule membrane component (A) is preferably 5 mass % or more, more preferably 8 mass % or more, still more preferably 10 mass % or more, still more preferably 15 mass % or more; the content is preferably 100 mass % or less, more preferably 85 mass % or less, still more preferably 70 mass % or less, still more preferably 60 mass % or less; and the content is preferably from 5 to 100 mass %, more preferably from 8 to 90 mass %, still more preferably from 10 to 70 mass %, still more preferably from 15 to 60 mass %.

<4> The solid composition described in any one of <1> to <3>, wherein the fat globule membrane component (A) preferably comprises sphingomyelin as a phospholipid, and a content of sphingomyelin in the fat globule membrane component is preferably 1 mass % or more, more preferably 2 mass % or more, still more preferably 3 mass % or more; the content is preferably 50 mass % or less, more preferably 30 mass % or less, still more preferably 25 mass % or less, still more preferably 20 mass % or less; and the content is preferably from 1 to 50 mass %, more preferably from 2 to 30 mass %, still more preferably from 3 to 25 mass %, still more preferably from 3 to 20 mass %.

<5> The solid composition described in any one of <1> to <4>, wherein a content of sphingomyelin in the total phospholipids of the fat globule membrane component (A) is preferably 3 mass % or more, more preferably 5 mass % or more, still more preferably 10 mass % or more, still more preferably 15 mass % or more; the content is preferably 50 mass % or less, more preferably 10 mass % or less, still more preferably 35 mass % or less, still more preferably 30 mass % or less; and the content is preferably from 3 to 50 mass %, more preferably from 5 to 40 mass %, still more preferably from 10 to 35 mass %, still more preferably from 15 to 30 mass %.

<6> The solid composition described in any one of <1> to <5>, wherein a content of the fat globule membrane component (A) in the solid composition is preferably 25 mass % or more, more preferably 30 mass % or more, still more preferably 35 mass % or more, still more preferably 40 mass % or more; the content is preferably 60 mass % or less, more preferably 55 mass % or less, still more preferably 50 mass % or less; and the content is preferably from 20 to 60 mass %, more preferably from 25 to 55 mass %, still more preferably from 30 to 50 mass %.

<7> The solid composition described in any one of <1> to <6>, wherein a content of phospholipid in the solid composition is preferably 1 mass % or more, more preferably 2 mass % or more, still more preferably 3 mass % or more, still more preferably 4 mass % or more; the content is preferably 60 mass % or less, more preferably 50 mass % or less, still more preferably 40 mass % or less, still more preferably 30 mass % or less; and the content is preferably from 1 to 60 mass %, more preferably from 2 to 50 mass %, still more: preferably from 3 to 40 mass %, still more preferably from 4 to 30 mass %.

<8> The solid composition described in any one of <1> to <7>, wherein a content of sphingomyelin in the solid composition is preferably 0.5 mass % or more, more preferably 0.7 mass % or more, still more preferably 1 mass % or more; the content is preferably 3.5 mass % or less, more preferably 3 mass % or less; and the content is preferably from 0.5 to 3.5 mass %, more preferably from 0.7 to 3.5 mass %, still more preferably from 1 to 3 mass %.

<9> The solid composition described in any one of <1> to <8>, wherein a weight average molecular weight of the water-soluble dietary fiber (B) is preferably 15,000 or more, and the weight average molecular weight is preferably 300,000 or less, more preferably 200,000 or less.

<10> The solid composition described in any one of <1> to <8>, wherein a weight average molecular weight of the water-soluble dietary fiber (B) is preferably from 10,000 to 300,000, more preferably from 15,000 to 250,000.

<11> The solid composition described in any one of <1> to <10>, wherein a content of the water-soluble dietary fiber (B) in the solid composition is preferably 0.3 mass % or more, more preferably 0.5 mass % or more; the content is preferably 3 mass % or less; and the content is preferably from 0.3 to 4 mass %, more preferably from 0.5 to 3 mass %.

<12> The solid composition described in any one of <1> to <11>, wherein a viscosity of the water-soluble dietary fiber (B) is preferably from 20 to 300 mPa·s, more preferably from 50 to 300 mPa·s.

<13> The solid composition described in any one <1> to <12>, wherein the water-soluble dietary fiber (B) is preferably one or more kinds selected from the group consisting of an acidic polysaccharide water-soluble dietary fiber and a neutral polysaccharide water-soluble dietary fiber; more preferably one or more kinds selected from the group consisting of alginic acid, carrageenan, polyglutamic acid, fucoidan, agaropectin, gum arable, karaya gum, gellan gum, xanthan gum, salts of these fibers, indigestible dextrin, guar gum, polydextrose, glucomannan, pullulan, water-soluble corn fiber, hemicellulose, soybean dietary fiber, and locust bean gum; still more preferably sodium alginate, guar gum, or pullulan; still more preferably guar gum or pullulan.

<14> The solid composition described, in any one of <1> to <12>> wherein the water-soluble dietary fiber (B) is preferably alginic acid or a salt thereof, more preferably alginic acid having a weight average molecular weight of from 20,000 to 80,000 or a salt thereof, still more preferably alginic acid having a weight average molecular weight of from 30,000 to 60,000 or a salt thereof.

<15> The solid composition described in any one of <1> to <12>, wherein the water-soluble dietary fiber (B) is preferably guar gum, more preferably guar gum having a weight average molecular weight, of from 100,000 to 300,000, still more preferably guar gum having a weight average molecular weight of from 150,000 to 250,000.

<16> The solid composition described in any one of <1> to <12>, wherein the water-soluble dietary fiber (B) is preferably a guar gum decomposition product, more preferably a guar gum decomposition product having a weight average molecular weight of from 10,000 to 50,000, still more preferably a guar gum decomposition product having a weight average molecular weight of from 15,000 to 30,000.

<17> The solid composition described in any one of <1> to <12>, wherein the water-soluble dietary fiber (B) is preferably pullulan, more preferably pullulan having a weight average molecular weight of from 30,000 to 100,000, still more preferably pullulan having a weight average molecular weight of from 40,000 to 85,000.

<18> The solid composition described, in any one of <1> to <17>, wherein a mass ratio of the content of the water-soluble dietary fiber having a weight average molecular weight of 10,000 or more (B) in the solid composition to the content of the fat globule membrane component (A) in the solid composition, [(B)/(A)], is preferably 0.004 or more, more preferably 0.0075 or more, still more preferably 0.01 or more; the mass ratio is preferably 0.15 or less, more preferably 0.1 or less, still more preferably 0.08 or less; and the mass ratio is preferably from 0.004 to 0.15, more preferably from 0.004 to 0.1, still, more preferably from 0.004 to 0.08, still more preferably from 0.01 to 0.08.

<19> The solid composition described in any one of <1> to <18>, wherein a form of the solid composition is a capsule, a granule, powder, a tablet, a pill, or a troche, more preferably a chewable tablet or a troche, still more preferably a chewable tablet.

EXAMPLES

[Analysis of Fat Globule Membrane Component]
(1) Analysis of Protein
The amount of protein was obtained using the Kjeldahl method while a nitrogen-protein conversion factor was set to 6.38.

(2) Analysis of Lipid
The amount of lipid was obtained by acid digestion. 1 g of a sample was weighed and decomposed by adding hydrochloric acid, then diethyl ether and petroleum ether were added thereto, and the resultant solution was stirred and mixed. An ether mixture layer was taken out and washed with water. After the solvent was distilled off and dried, the weight was measured to obtain the amount of lipid.

(3) Analysis of Carbohydrate
The amount of carbohydrate was obtained by subtracting the protein amount, the lipid mass, the ash content, and the moisture amount from the mass of the sample. Incidentally, the ash content was obtained by a direct ashing method (the sample was subjected to ashing at 550° C. and then the weight thereof was measured), and the moisture amount was obtained by a normal-pressure heat-drying method (the sample was dried at 105° C. for 4 hours and then the weight thereof was measured).

(4) Analysis of Phospholipid
1 g of a sample was weighed and homogenised in 150 mL, 100 mL, and 20 mL of mixed solutions of chloroform and methanol (2:1 (V/V)), 93 mL of 0.88% (W/V) potassium chloride aqueous solution was then added thereto, and the resultant solution was left to stand at room temperature overnight. After dehydration and filtration were performed and the solvent was distilled off, chloroform was added thereto so that the resultant solution had a total amount of 50 mL. After 2 mL of the solution was fractionated and the solvent was distilled off, heat treatment was carried, out at 550° C. for 1.6 hours to perform ashing. The ash was dissolved in 5 mL of 6M hydrochloric acid aqueous solution, and then distilled water was added thereto so that the resultant solution had a total amount of 50 mL. 3 mL of the solution was fractionated, 5 mL of molybdenum blue coloring reagent, 1 mL of 5% (W/V) ascorbic acid aqueous solution, and distilled water were added thereto so that the resultant solution had a total amount of 50 mL, and then the absorbance at 710 nm was measured. The phosphorus amount was obtained from a calibration curve using potassium dihydrogenphosphate and a value obtained by multiplying the phosphorus amount by 25.4 was designated as the phospholipid amount.

(5) Analysis of Sphingomyelin
1 g of a sample was weighed and homogenized in 150 mL, 100 mL, and 20 mL of mixed solutions of chloroform and methanol (2:1 (V/V)), 93 mL of 0.88% (W/V) potassium chloride aqueous solution was then added thereto, and the resultant solution was left to stand at room temperature overnight. After dehydration and filtration were performed and the solvent was distilled off, chloroform was added thereto so that the resultant solution had a total amount of 53 mL. 10 mL of the solution was fractionated and added to a silica cartridge column. After the column was washed with 20 mL of chloroform, phospholipid was eluted with 30 mL of methanol. After the solvent was distilled off, the resultant was dissolved in 1.88 mL of chloroform. A load of 20 μL was applied to the silica gel thin layer plate, and two-dimensional development was performed using tetrahydrofuran:acetone:methanol:water=50:28:40:8 (V/V) as a one-dimensional developing solvent and chloroform:acetone:methanol:acetic acid:water=50:20:10:15:5 (V/V) as a two-dimensional developing solvent. The Dittmer's reagent was sprayed to the developed thin layer plate, the spot of sphingomyelin was scraped, 2 mL of 3% (V/V) nitric acid containing-perchloric acid solution was then added thereto, and heat treatment was carried out at 170° C. for 3 hours. After 5 mL of distilled water was added thereto, 5 mL of molybdenum blue coloring reagent, 1 mL of 5% (W/V) ascorbic acid aqueous solution, and distilled water were added thereto so that the resultant solution had a total amount of 50 mL, and then the absorbance at 710 nm was measured. The phosphorus amount was obtained from a calibration curve using potassium dihydrogenphosphate and a value obtained by multiplying the phosphorus amount by 25.4 was designated as the sphingomyelin amount.

[Measurement of height Average Molecular Weight by GPC Method]

The weight average molecular weight of the water-soluble dietary fiber was measured by high performance liquid chromatography (HPLC). The HPLC operation conditions are as follows. To obtain a calibration curve for calculating a molecular weight, standard pullulan (Shodex: STANDARD P-82 produced by SHOW A DENKO K.K.) was used. A 100 µL analytical sample for HPLC was injected to HPLC, and the weight average molecular weight of the water-soluble dietary fiber in the sample was calculated from the obtained chromatogram chart.

Column: Super AW-L (guard column) manufactured by Tosoh Corporation)

TSK-GEL Super AW4000 (length: 15 cm, inner diameter: 6 mm) (manufactured by Tosoh Corporation)

TSK-GEL Super AW2500 (length: 15 cm, inner diameter; 6 mm) (manufactured by Tosoh Corporation)

* The above-described columns were connected in the order of AW-L, AW4000, and AW2500.

Column temperature: 40° C.

Detector: differential refractormeter

Mobile phase: 0.2 mol/L of sodium nitrate aqueous solution

Flow rate: 0.6 mL/min

Injection amount: 100 µL

[Measurement of Viscosity]

The viscosity of the water-soluble dietary fiber was measured using a B-type viscometer (rotor: No. 4, revolution speed; 100 revolutions/min) manufactured by BROOK FIELD Ltd. after the initial temperature of an aqueous solution prepared by dissolving 10 g of the water-soluble dietary fiber in 90 g of ion water was adjusted to 20° C.

[Raw Material]

Fat globule membrane component 1: BSCP, produced by MEGGLE JAPAN CO., LTD.

Fat globule membrane component 2: Milk Ceramide MC-5, produced by Snow Brand Milk Products Co., Ltd., Pullulan: weight average molecular weight of 70,000, viscosity of 132 mPa·s, produced by HAYASHIBARA CO., LTD.

Guar gum: weight average molecular weight of 200,000, viscosity of 289 mPa·s, produced by Taiyo Kagaku Co., Ltd.

Guar gum decomposition product: weight average molecular weight of 20,000, viscosity of 26 mPa·s, produced by Taiyo Kagaku Co., Ltd.

Sodium alginate: weight average molecular weight of 45,000, viscosity of 56 mPa·s, produced by KIMICA Corporation Dextrin: weight average molecular weight of 8,500, viscosity of 10 mPa·s, produced by Matsutani Chemical Industry Co., Ltd.

Polydextrose: weight average molecular weight of 2,000, viscosity of 4 mPa·s, produced, by TAKEDA-KIRIN FOODS CORPORATION Indigestible dextrin: weight average molecular weight of 2,000, viscosity of 4 mPa·s, produced by Matsutani Chemical Industry Co., Ltd.

Corn starch: Nisshoku Corn Starch, produced by NIHON SHOKUHIN KAKO CO., LTD.

Aspartame: PAL SWEET DIET, produced by Ajinomoto Co., Inc.

Crystalline cellulose: KC FLOCK W-400G, produced by Nippon Paper Chemicals Co., Ltd.

Maltitol: Amalty MR-100, produced by Mitsubishi Shoji Foodtech Co., Ltd.

The composition of the fat globule membrane component 1 was carbohydrate; 10.7%, lipid: 23.8%, and protein: 50.9% in terms of dry matter. Further, the content of phospholipid in the fat globule membrane component 1 was 16.6%. The content of sphingomyelin was 3.62%.

The composition of the fat globule membrane component 2 was carbohydrate: 26.1%, lipid; 43.3%, and protein: 21.2% in terms of dry matter. Further, the content of phospholipid in the fat globule membrane component 2 was 33.3%. The content of sphingomyelin was 8.03%.

Preparation of Chewable Tablet

Example 1 to Example 10 and Comparative Example 1 to Comparative Example 8

A raw material having a large particle diameter was pulverized and was passed through a 50-mesh screen and each raw material component was mixed at the blend composition described in Table 1. Next, chewable tablets, each of 500 mg weight, were obtained using a single punch tableting machine (manufactured by RIKEN, Japan) with a ring-form punch having a hole diameter of 9.5 mm.

The inventive products and comparative products obtained above were subjected to sensory evaluation. The evaluation was first performed on all samples in the following way; two specialized panelists ate the samples, and evaluated them for the texture, the milk flavor derived from the fat globule membrane component, and the sour taste according to the determination criteria described below; and the example with the highest evaluation was rated as "5" while the example with the lowest evaluation was rated as "1". Then, relative rating with a five-step scale among "1" to "5" was performed on other samples. The average value of the scores from two panelists was used as a mark (rounding-off by 0.5 points in unit). The results thereof are presented in Table 1.

[Texture]

The evaluation was carried out when Example 2 was rated as "5" and Comparative Example 8 was rated as "1". Specifically, the evaluation was carried cut based on items as described below.

5: Favorable crispy texture without dry texture is sensed and melt-in-the-mouth texture is very favorable.

4: Dry texture is sensed hardly, favorable crispy texture is sensed slightly, and melt-in-the-mouth texture is favorable.

3: Dry texture is sensed slightly, favorable crispy texture is sensed to some degree, and melt-in-the-mouth texture is slightly favorable.

2: Dry texture is sensed, crispy texture is sensed hardly, and melt-in-the-mouth texture is slightly poor.

1: Dry texture is sensed strongly, crispy texture is not sensed, and melt-in-the-mouth texture is poor.

[Milk Flavor Derived from Fat Globule Membrane Component]

The evaluation was carried out when Example 2 was rated as "5" and Comparative Example 7 was rated as "1". Specifically, the evaluation was carried out based on items as described below.

5: Favorable milk flavor is sensed very strongly.
4: Favorable milk flavor is sensed strongly.
3: Favorable milk flavor is sensed.
2: Favorable milk flavor is sensed hardly.
1: No favorable milk flavor is sensed.

[Sour Taste]

The evaluation was carried out when Example 2 was rated as "5" and Comparative Example 8 was rated as "1". Specifically, the evaluation was carried out based on items as described below.

5: Favorable sour taste is sensed very strongly.
4: Favorable sour taste is sensed.
3: Favorable sour taste is sensed slightly.
2: Favorable sour taste is sensed hardly.
1: No favorable sour taste is sensed.

TABLE 1

| (mass %) | | Example 1 | Example 2 | Example 3 | Example 4 | Example 5 | Example 6 | Example 7 | Example 8 | Example 9 | Example 10 | Comparative Example 1 | Comparative Example 2 | Comparative Example 3 | Comparative Example 4 | Comparative Example 5 | Comparative Example 6 | Comparative Example 7 | Comparative Example 8 |
|---|---|---|---|---|---|---|---|---|---|---|---|---|---|---|---|---|---|---|---|
| (A) | Fat globule membrane component 1 | 40.0 | 40.0 | 40.0 | 40.0 | 20.0 | 65.0 | 40.0 | 40.0 | 40.0 | — | 40.0 | 40.0 | 40.0 | 40.0 | 40.0 | 40.0 | 10.0 | 70.0 |
| | Fat globule membrane component 2 | — | — | — | — | — | — | — | — | — | 40.0 | — | — | — | — | — | — | — | — |
| (B) | Pullulan (molecular weight: 70,000) | 0.3 | 0.5 | 1.0 | 3.0 | 0.5 | 0.5 | — | — | — | 0.5 | — | — | — | — | 0.1 | 5.0 | 0.5 | 0.5 |
| | Guar gum (molecular weight: 200,000) | — | — | — | — | — | — | 0.5 | — | — | — | — | — | — | — | — | — | — | — |
| | Sodium alginate (molecular weight: 45,000) | — | — | — | — | — | — | — | 0.5 | — | — | — | — | — | — | — | — | — | — |
| | Guar gum decomposition product (molecular weight: 20,000) | — | — | — | — | — | — | — | — | 0.5 | — | — | — | — | — | — | — | — | — |
| | (B)/(A) | 0.008 | 0.013 | 0.025 | 0.075 | 0.025 | 0.008 | 0.013 | 0.013 | 0.013 | 0.013 | 0.000 | 0.000 | 0.000 | 0.000 | 0.003 | 0.125 | 0.050 | 0.007 |
| | Dextrin (molecular weight: 8,500) | — | — | — | — | — | — | — | — | — | — | — | 0.5 | — | — | — | — | — | — |
| | Polydextrose (molecular weight: 2,000) | — | — | — | — | — | — | — | — | — | — | — | — | 0.5 | — | — | — | — | — |
| | Indigestible dextrin (molecular weight: 2,000) | — | — | — | — | — | — | — | — | — | — | — | — | — | 0.5 | — | — | — | — |
| | Corn starch | 48.7 | 48.5 | 48.0 | 46.0 | 68.5 | 23.5 | 48.5 | 48.5 | 48.5 | 48.5 | 49.0 | 48.5 | 48.5 | 48.5 | 48.9 | 44.0 | 78.5 | 18.5 |
| | Aspartame | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 |
| | Crystalline cellulose | 5.0 | 5.0 | 5.0 | 5.0 | 5.0 | 5.0 | 5.0 | 5.0 | 5.0 | 5.0 | 5.0 | 5.0 | 5.0 | 5.0 | 5.0 | 5.0 | 5.0 | 5.0 |
| | Maltitol | 5.0 | 5.0 | 5.0 | 5.0 | 5.0 | 5.0 | 5.0 | 5.0 | 5.0 | 5.0 | 5.0 | 5.0 | 5.0 | 5.0 | 5.0 | 5.0 | 5.0 | 5.0 |
| | Total | 100.0 | 100.0 | 100.0 | 100.0 | 100.0 | 100.0 | 100.0 | 100.0 | 100.0 | 100.0 | 100.0 | 100.0 | 100.0 | 100.0 | 100.0 | 100.0 | 100.0 | 100.0 |
| Evaluation item | Texture | 4.5 | 5.0 | 4.0 | 3.5 | 5.0 | 3.0 | 5.0 | 4.5 | 4.0 | 4.0 | 1.5 | 2.0 | 2.0 | 1.5 | 2.5 | 2.0 | 2.0 | 1.0 |
| | Milk flavor | 4.5 | 5.0 | 4.5 | 4.0 | 3.0 | 5.0 | 4.5 | 4.0 | 3.5 | 4.0 | 1.5 | 2.5 | 2.0 | 2.0 | 3.5 | 2.5 | 1.0 | 4.5 |
| | Sour taste | 4.0 | 5.0 | 4.0 | 4.0 | 3.5 | 4.0 | 4.5 | 3.5 | 3.5 | 4.0 | 1.5 | 2.0 | 2.0 | 1.5 | 2.5 | 1.5 | 2.5 | 1.0 |

As clearly seen from Table 1, Comparative Example 1 in which the water-soluble dietary fiber was not blended had a dry texture and was crumbly and poor in the melt-in-the-mouth texture, and a favorable milk flavor intrinsic to the fat globule membrane component and sour taste were not sensed. Although the dextrin (Comparative Example 2) or the water-soluble dietary fiber having a weight average molecular weight of less than 10,000 (Comparative Examples 3 and 4) was blended, the above-described problems were not improved.

To the contrary, Examples 1 to 10 in which a predetermined amount of the water-soluble dietary fiber having a weight average molecular weight of 10,000 or more was blended had no dry texture and were crispy and excellent in the melt-in-the-mouth texture, and a favorable milk flavor intrinsic to the fat globule membrane component and sour taste were strongly sensed so that the flavor was good.

Comparative Examples 5 and 6 in which a predetermined amount of the water-soluble dietary fiber having a weight average molecular weight of 10,000 or more was not blended, Comparative Example 7 in which the proportion of the fat globule membrane component was small, and Comparative Example 8 in which the proportion of the fat globule membrane component was large had a poor texture.

The invention claimed is:

1. A solid composition comprising the following components (A) and (B):
   (A) from 20 to 65 mass % of a fat globule membrane component; and
   (B) from 0.3 to 3 mass % of at least one water-soluble dietary fiber selected from the group consisting of sodium alginate having a weight average molecular weight of from 30,000 to 80,000 g/mol, pullulan having a weight average molecular weight of from 40,000 to 85,000 g/mol, guar gum having a weight average molecular weight of 150,000 to 250,000 g/mol and a guar gum decomposition product having a weight average molecular weight of 15,000 to 30,000 g/mol.

2. The solid composition according to claim 1, wherein a mass ratio of a content of the component (B) to a content of the component (A), [(B)/(A)], is from 0.0075 to 0.08.

3. The solid composition according to claim 2, wherein a content of phospholipid in the solid composition is from 1 to 60 mass %.

4. The solid composition according to claim 2, wherein a content of sphingomyelin in the solid composition is from 0.5 to 3.5 mass %.

5. The solid composition according to claim 2, wherein the solid composition is a chewable tablet.

6. The solid composition according to claim 1, wherein the solid composition is a tablet.

7. The solid composition according to claim 1, wherein the solid composition is a form selected from the group consisting of a capsule, a granule, a powder, a pill, and a troche.

8. The solid composition according to claim 1, wherein:
   a mass ratio of a content of the component (B) to a content of the component (A), [(B)/(A)], is from 0.0075 to 0.08;
   a content of phospholipid in the solid composition is from 1 to 60 mass %; and
   a content of sphingomyelin in the solid composition is from 0.5 to 3.5 mass %.

9. The solid composition according to claim 8, wherein the solid composition is a tablet.

10. The solid composition according to claim 9, wherein the solid composition is a chewable tablet.

11. The solid composition according to claim 1, wherein a content of phospholipid in the solid composition is from 1 to 60 mass %.

12. The solid composition according to claim 11, wherein a content of sphingomyelin in the solid composition s from 0.5 to 3.5 mass %.

13. The solid composition according to claim 11, wherein the solid composition is a chewable tablet.

14. The solid composition according to claim 1, wherein a content of sphingomyelin in the solid composition is from 0.5 to 3.5 mass %.

15. The solid composition according to claim 14, wherein h solid composition is a chewable tablet.

16. The solid composition according to claim 1, wherein the solid composition is a chewable tablet.

* * * * *